(12) United States Patent
    Lin

(10) Patent No.: US 11,105,003 B2
(45) Date of Patent: Aug. 31, 2021

(54) WATER ELECTROLYSIS DEVICE

(71) Applicant: Hsin-Yung Lin, Shanghai (CN)

(72) Inventor: Hsin-Yung Lin, Shanghai (CN)

( * ) Notice: Subject to any disclaimer, the term of this patent is extended or adjusted under 35 U.S.C. 154(b) by 242 days.

(21) Appl. No.: 16/108,769

(22) Filed: Aug. 22, 2018

(65) Prior Publication Data

US 2019/0062933 A1 Feb. 28, 2019

(30) Foreign Application Priority Data

Aug. 25, 2017 (CN) .......................... 201710739861.5

(51) Int. Cl.

| C25B 1/04 | (2021.01) |
|---|---|
| A61M 16/10 | (2006.01) |
| C25B 15/08 | (2006.01) |
| C25B 9/73 | (2021.01) |
| C25B 9/23 | (2021.01) |
| C25B 11/04 | (2021.01) |
| G01N 33/18 | (2006.01) |

(Continued)

(52) U.S. Cl.
CPC .............. *C25B 1/04* (2013.01); *A61M 16/101* (2014.02); *C25B 9/23* (2021.01); *C25B 9/73* (2021.01); *C25B 11/04* (2013.01); *C25B 15/08* (2013.01); *G01N 33/18* (2013.01); *A61M 11/044* (2014.02); *A61M 16/162* (2013.01); *A61M 2202/02* (2013.01); *Y02E 60/36* (2013.01)

(58) Field of Classification Search
CPC .................................................. C25B 1/02–12
See application file for complete search history.

(56) References Cited

U.S. PATENT DOCUMENTS

| 4,107,008 A | 8/1978 | Horvath |
| 4,369,737 A | 1/1983 | Sanders et al. |

(Continued)

FOREIGN PATENT DOCUMENTS

| CN | 103670808 A | * | 3/2014 | ............. F02M 21/04 |
| CN | 105498065 A | | 4/2016 | |

(Continued)

OTHER PUBLICATIONS

Extended Search Report dated May 15, 2019 for European Application No. 18189192.0.

(Continued)

*Primary Examiner* — Nicholas A Smith

(57) ABSTRACT

A water electrolysis device comprises an ion exchange membrane electrolytic cell. The ion exchange membrane electrolytic cell includes an ion exchange membrane, a cathode chamber, an anode chamber, a hydrogen output tube, and an oxygen output tube. An anode is configured in the anode chamber, and a cathode is configured in the cathode chamber. The ion exchange membrane is configured between the anode chamber and the anode chamber. The hydrogen output tube is coupled to the cathode chamber, and the oxygen output tube is coupled to the anode chamber. When water is electrolyzed by the ion exchange membrane electrolytic cell, oxygen is generated by the anode and then exported through the oxygen output tube, and hydrogen is generated by the cathode and then exported through the hydrogen output tube. The hydrogen and the oxygen are exported from the same side of the ion exchange membrane electrolytic cell.

20 Claims, 13 Drawing Sheets

(51) Int. Cl.
*A61M 11/04* (2006.01)
*A61M 16/16* (2006.01)

(56) References Cited

U.S. PATENT DOCUMENTS

| | | |
|---|---|---|
| 5,037,518 A | 8/1991 | Young et al. |
| 2002/0090868 A1* | 7/2002 | Schmitman ............ C01B 3/001 440/113 |
| 2003/0051997 A1 | 3/2003 | Lin et al. |
| 2010/0206740 A1 | 8/2010 | Takeuchi et al. |
| 2011/0132748 A1 | 6/2011 | Haryu et al. |
| 2011/0147202 A1 | 6/2011 | Haryu et al. |
| 2011/0229780 A1* | 9/2011 | Kershaw ........... H01M 8/04626 429/422 |
| 2012/0073525 A1* | 3/2012 | Owens .................. H01M 8/00 123/3 |
| 2014/0048067 A1* | 2/2014 | McGill ............ A61M 15/0086 128/203.29 |
| 2014/0374243 A1* | 12/2014 | Lin ......................... C25B 9/06 204/228.3 |
| 2015/0101601 A1* | 4/2015 | Lin ......................... C25B 1/04 128/202.26 |
| 2015/0292091 A1* | 10/2015 | Satoh ...................... C25B 9/08 204/265 |
| 2016/0108528 A1 | 4/2016 | Lin |
| 2016/0263341 A1 | 9/2016 | Lin |
| 2017/0327960 A1* | 11/2017 | Kurashina ................ C25B 1/04 |
| 2018/0320275 A1 | 11/2018 | Lin |

FOREIGN PATENT DOCUMENTS

| | | | |
|---|---|---|---|
| CN | 205649716 | 10/2016 | |
| CN | 106906483 A | 6/2017 | |
| CN | 107041988 | 8/2017 | |
| JP | 08-239788 * | 9/1996 | ............... C25B 9/00 |
| JP | 2862808 B2 | 9/1996 | |
| JP | H08239788 A | 9/1996 | |
| JP | 2002269633 | 9/2002 | |
| JP | 2006131957 | 5/2006 | |
| JP | 2010189728 A | 9/2010 | |
| JP | 2011208259 | 10/2011 | |
| JP | 2016180177 A | 10/2016 | |
| JP | 2017012501 | 1/2017 | |
| TW | 201723233 | 7/2017 | |
| TW | M554472 | 1/2018 | |
| WO | WO2014007802 A1 | 1/2014 | |

OTHER PUBLICATIONS

Office Action dated Jun. 6, 2019 for Australian Application No. 2018217248.
Office Action dated Aug. 6, 2019 for Canadian Application No. 3,014,948.
Search Report and Written Opinion dated Jan. 24, 2019 for Singapore Application No. 10201807058X.
Examination Report dated Dec. 6, 2019 for Philippines Application 1/2018/000230.
Examination Report dated Nov. 20, 2019 for Indian Application 201824030730.

* cited by examiner

WATER ELECTROLYSIS DEVICE

CROSS-REFERENCE TO RELATED APPLICATIONS

This application claims the priority benefit of Chinese Application Serial No. 201710739861.5 filed Aug. 25, 2017 the disclosure of which is incorporated herein by reference.

BACKGROUND OF THE INVENTION

Field of the Invention

The present invention provides a water electrolysis device, more particularly, to a water electrolysis device comprising an ion exchange membrane electrolytic cell outputting hydrogen and oxygen from the same side.

Description of the Prior

As people have always been paying much attention on health developments, many developments in medical technology are often targeted on treating diseases and prolonging human life. Most of the treatments in the past are passive, which means that the disease is treated only when it occurs. The treatments include an operation, a medication treatment, a radiation therapy, or even a medical treatment for cancer. However, in recent years, most of the researches from medical experts are gradually moving towards preventive medical methods, such as research on healthy food, screening and the prevention of inherited diseases, which actively prevents diseases from occurring in the future. Due to the focus of the prolongation of human life, many anti-aging and anti-oxidation technologies including skin care products and anti-oxidation food/medicine are gradually being developed and becoming increasingly popular to the general public.

Studies have found that there are instable oxygen species (O+), also known as free radicals, in the human body. The free radicals which are usually generated due to diseases, diet, environment or one's lifestyle can be excreted in the form of water by reacting with the inhaled hydrogen. With this method, the amount of free radicals in the human body can be reduced, thereby restoring the body condition from an acidic state to an alkaline state, achieving an anti-oxidation, anti-aging and beauty health effect, and even eliminating chronic diseases. Furthermore, there are also clinical experiments showing that patients who need to inhale a high concentration of oxygen for an extended period of time would experience lung damage, but the lung damage could be ameliorated by inhaling hydrogen.

In order to enhance the efficacy of inhaling hydrogen, increasing the time of inhaling hydrogen is an effective method. However, the electrolysis device is bulky in prior art; moreover, it is not easy to arrange enough daytime to inhale hydrogen. Therefore, the use of sleeping-time to inhale hydrogen would be an effective way. However, as mentioned above, the conventional electrolysis device is bulky. How to reduce the volume of the electrolysis device and maintain a sufficient quantity of hydrogen is a problem waiting to be solved.

In addition to the health care, the hydrogen also can be used to generate hydrogen flame to heat or burn, or to remove the engine carbon deposits. In general, hydrogen is generated by electrolyzing the electrolyte water along with the high working temperature. And, the temperature of the electrolysis device is cooling down by fan. Once there is something wrong with the fan, the hydrogen explosion might be happened. Besides, the gas generated by the electrolysis device usually has the electrolyte which is not suitable for inhaling. At the same time, the electrolyte will be lost during the electrolyzation.

SUMMARY OF THE INVENTION

In response to the above-mentioned problems, an object of the present invention is to provide a water electrolysis device.

The present invention provides a water electrolysis device, comprising a housing and an ion exchange membrane electrolytic cell. The housing comprises a side wall. The ion exchange membrane electrolytic cell is configured at a non-center within the housing. The ion exchange membrane electrolytic cell comprises a first side, a second side corresponding to the first side, an ion exchange membrane, a cathode, an anode, a hydrogen output tube, and an oxygen output tube. The ion exchange membrane is configured between the cathode and the anode. Wherein, when the ion exchange membrane electrolytic cell electrolyzes water, the cathode generates hydrogen, and the hydrogen is outputted via the hydrogen output tube. The anode generates oxygen, and the oxygen is outputted via the oxygen output tube. Wherein the first side faces the side wall, and the hydrogen and the oxygen are outputted from the second side of the ion exchange membrane electrolytic cell.

In an embodiment, the anode is configured between the ion exchange membrane and the second side. The cathode is configured between the ion exchange membrane and the first side. The oxygen output tube extends from the area between the ion exchange membrane and the second side to the second side, and penetrates through the second side. The hydrogen output tube extends from the area between the ion exchange membrane and the first side to the second side, and penetrates through the second side.

In an embodiment, the anode is configured between the ion exchange membrane and the first side. The cathode is located between the ion exchange membrane and the second side. The hydrogen output tube extends from the area between the ion exchange membrane and the second side, and penetrates through the second side. The oxygen output tube extends from the area between the ion exchange membrane and the first side, and penetrates through the first side.

In an embodiment, the ion exchange membrane electrolytic cell comprises a cathode chamber and an anode chamber. The cathode chamber comprises the cathode, a cathode seal plate, a cathode conductive plate, and a cathode external plate. The anode chamber comprises the anode, an anode seal plate, an anode conductive plate, and an anode external plate.

In an embodiment, the ion exchange membrane electrolytic cell further comprises a water tube penetrating through the cathode external plate, the cathode conductive plate, and the cathode seal plate for communicating the cathode chamber and a water tank. The water of the water tank flows into the cathode chamber via the water tube for replenishing the cathode chamber.

In an embodiment, the electrolysis device further comprises a gas tube, a fan, and a gas pump. Wherein, the gas tube is coupled to hydrogen output tube for receiving the hydrogen. The fan draws the air from external environment out of the electrolysis device into the electrolysis device, and the gas pump draws the air into the gas tube for diluting the hydrogen concentration inside the gas tube.

In an embodiment, the electrolysis device further comprising a gas mixing chamber coupled to the gas tube for receiving the diluted hydrogen. Wherein the gas mixing chamber selectively generates an atomized gas for mixing with the hydrogen to form a healthy gas, and the atomized gas is one selected from a group consisting of water vapor, atomized solution, volatile essential oil, and any combination thereof.

In an embodiment, the gas pump is coupled to the gas tube via a gas inlet, and a linking position between the gas inlet and the gas tube is provided with an angle, and the angle is less than 90 degrees. In another embodiment, the angle is in a range between 25 degrees and 45 degrees, and the shape of the linking position with the angle is made into an arc angle.

The electrolysis device of claim may further comprise a hydrogen concentration detector and a controller. The hydrogen concentration detector is coupled to the gas tube and is for detecting whether the hydrogen concentration of the gas tube is in a range between a first threshold and a second threshold. Wherein, the hydrogen concentration detector generates a first warning signal when the detected hydrogen concentration is higher than the first threshold. The controller is coupled to the hydrogen concentration detector, the gas pump, and the ion exchange membrane electrolytic cell. Wherein, the controller generates a start command for turning on the gas pump when receiving the first warning signal.

In an embodiment, the hydrogen concentration detector generates a second warning signal when the detected hydrogen concentration is higher than the second threshold. The controller generates a stop command for turning off the ion exchange membrane electrolytic cell when receiving the second warning signal. The first threshold is 4%, the second threshold is 6%, and the range is from 4% to 6%.

In an embodiment, the ion exchange membrane comprises a membrane body, a cathode catalyst layer, and an anode catalyst layer, the cathode catalyst layer. The anode catalyst layers are respectively located at two sides of the membrane body, the cathode catalyst layer is located at the cathode chamber, and the anode catalyst layer is located at the anode chamber. The anode catalyst layer is one selected from a group consisting of Pt, Ir, Pd, the alloy powder of Pt, carbon, and combinations thereof; the cathode catalyst layer is one selected from a group consisting of Pt, Ir, Pd, the alloy powder of Pt, and combinations thereof, and the membrane body is a Nafion membrane.

In an embodiment, the electrolysis device further comprises a water gauge for detecting water level of the water tank.

The electrolysis device may further comprise a power supplier. Wherein, the power supplier comprises a high power port and a low power port. The electric power outputted from the low power port is less than 50% of the electric power outputted from the high power port. The high power port outputs a first voltage and a first current, and the low power port outputs a second voltage and a second current. The first voltage is less than the second voltage, and the first current is greater than the second current.

In an embodiment, the electrolysis device may further comprises an operation panel; wherein, the volume of the electrolysis device is less than 8.5 liters, and a hydrogen production rate of the electrolysis device regulated by the operation panel is in a range between 120 mL/min to 600 mL/min.

The present invention also provides another electrolysis device comprising a water tank, an ion exchange membrane electrolytic cell, and a pre-heating tank. The water tank accommodates water. The ion exchange membrane electrolytic cell receives the water from the water tank. Wherein, the ion exchange membrane electrolytic cell comprises an ion exchange membrane, a cathode, an anode, a hydrogen output tube, and an oxygen output tube. When the ion exchange membrane electrolytic cell electrolyzes the water, the cathode generates hydrogen and the anode generates oxygen, the hydrogen output tube is used for outputting the hydrogen, and the oxygen output tube is used for outputting the oxygen and the remained water.

The pre-heating tank comprises a water inlet, a water outlet, and an oxygen import tube. The water inlet is coupled to the water tank for receiving the water. The water is outputted to the ion exchange membrane electrolytic cell from the water outlet. The oxygen import tube is coupled to the oxygen output tube, and the water with high temperature remained after electrolyzing and the oxygen being outputted to the pre-heating tank via the oxygen import tube. Wherein, the oxygen and the hydrogen are outputted from the same side of the ion exchange membrane electrolytic cell. The water with high temperature outputted from the oxygen import tube pre-heats the water of the pre-heating tank.

The water of the pre-heating tank is pre-heat to the temperature between 55° C. and 65° C., and the volume of the pre-heating tank is less than that of the water tank.

In an embodiment, the pre-heating tank further comprises a plurality of cooling fins and a second fan; the cooling fins are radially configured on an outside wall of the pre-heating tank, and the second fan is configured on an end of the pre-heating tank for cooling the pre-heating tank.

The present invention further provides another electrolysis device comprising an ion exchange membrane electrolytic cell and an integrated pathway module. The ion exchange membrane electrolytic cell is configured for electrolyzing water. The ion exchange membrane electrolytic cell comprises a second side, an ion exchange membrane, a cathode, an anode, a hydrogen output tube, and an oxygen output tube. Wherein, the ion exchange membrane is configured between the cathode and the anode. Wherein, when the ion exchange membrane electrolytic cell electrolyzes water, the cathode generates hydrogen, and the hydrogen is outputted via the hydrogen output tube, the anode generates oxygen, and the oxygen is outputted via the oxygen output tube. The integrated pathway module has a water tank and a gas pathway. The water tank is coupled to the ion exchange membrane electrolytic cell for replenishing the water to the ion exchange membrane electrolytic cell. Wherein, the top of the water tank is higher than the top of the ion exchange membrane electrolytic cell. The gas pathway is coupled to the ion exchange membrane electrolytic cell for transporting the hydrogen. Wherein, the second side of the ion exchange membrane electrolytic cell faces the integrated pathway module. The oxygen and the hydrogen are outputted to the gas pathway from the second side. The water is inputted to the ion exchange membrane electrolytic cell from the second side.

Compare to the prior art, the ion exchange membrane electrolytic cell outputs the hydrogen and the oxygen at the same side. Furthermore, the ion exchange membrane electrolytic cell, the water tank, the gas tube, the fan, the gas pump, the operation panel, the gas mixing chamber, and other devices are configured in the housing within the limited volume. Therefore, the present invention maintains enough hydrogen production and also provides accommodation space within the housing as much as possible. The present invention provides a water electrolysis device which is efficient in using space, small size and low noise, so the electrolysis device can be used conveniently by the user.

BRIEF DESCRIPTION OF THE APPENDED DRAWINGS

Some of the embodiments will be described in detail, with reference to the following figures, wherein like designations denote like members, wherein.

The advantages, spirits, and features of the present invention will be explained and discussed with embodiments and figures as follows.

DETAILED DESCRIPTION OF THE INVENTION

A detailed description of the hereinafter described embodiments of the disclosed apparatus and method are presented herein by way of exemplification and not limitation with reference to the Figures. Although certain embodiments are shown and described in detail, it should be understood that various changes and modifications can be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

In the description of the present specification, the terminologies "in an embodiment", "in another embodiment", or "in some embodiments" means that the specific feature, structure, material or characteristic of the present embodiment is involved in at least one embodiment of the present invention. In the description of the present specification, the schematic representation of the mentioned terminologies does not necessarily refer to the same embodiment. Furthermore, the described specific feature, structure, material or characteristic can be involved in any one or more embodiments in a proper way.

In the embodiments of the present specification, the terminology "or" includes the combination of part of listed components, and the combination of all the listed components. For example, the described "A or B" includes only A, only B, and both A and B. Moreover, the terminologies "a" and "the" before the element or component of the present invention do not limit the number of element or component. Therefore, the terminologies "a" and "the" should be read as including one or at least one. Besides, the singular form of element or component also includes the plural form, unless the number clearly refers to the singular form.

Figure 1A:
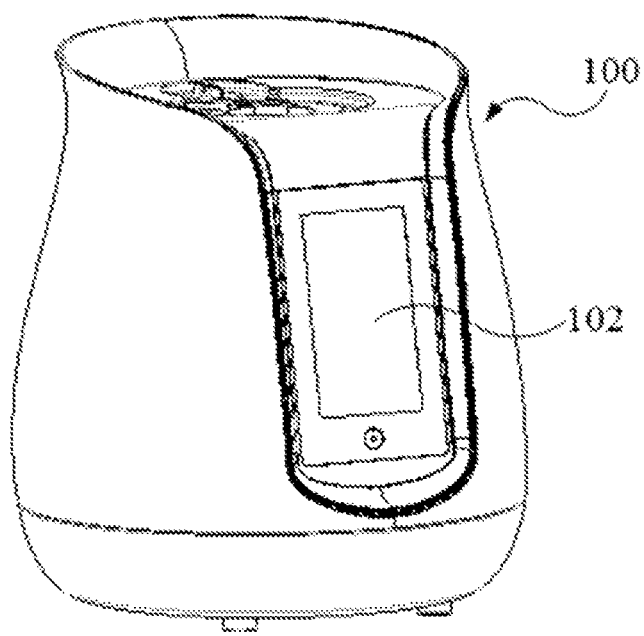
FIG. 1A shows an appearance view of one embodiment of the electrolysis device in the present invention.
Figure 1B:
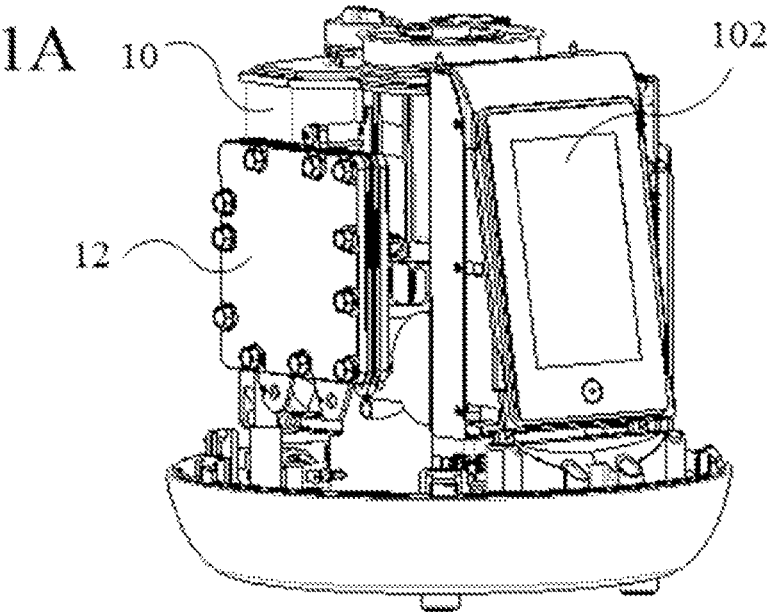
FIG. 1B shows an appearance view of the electrolysis device without the shell of FIG. 1A in the present invention.
Figure 1C:
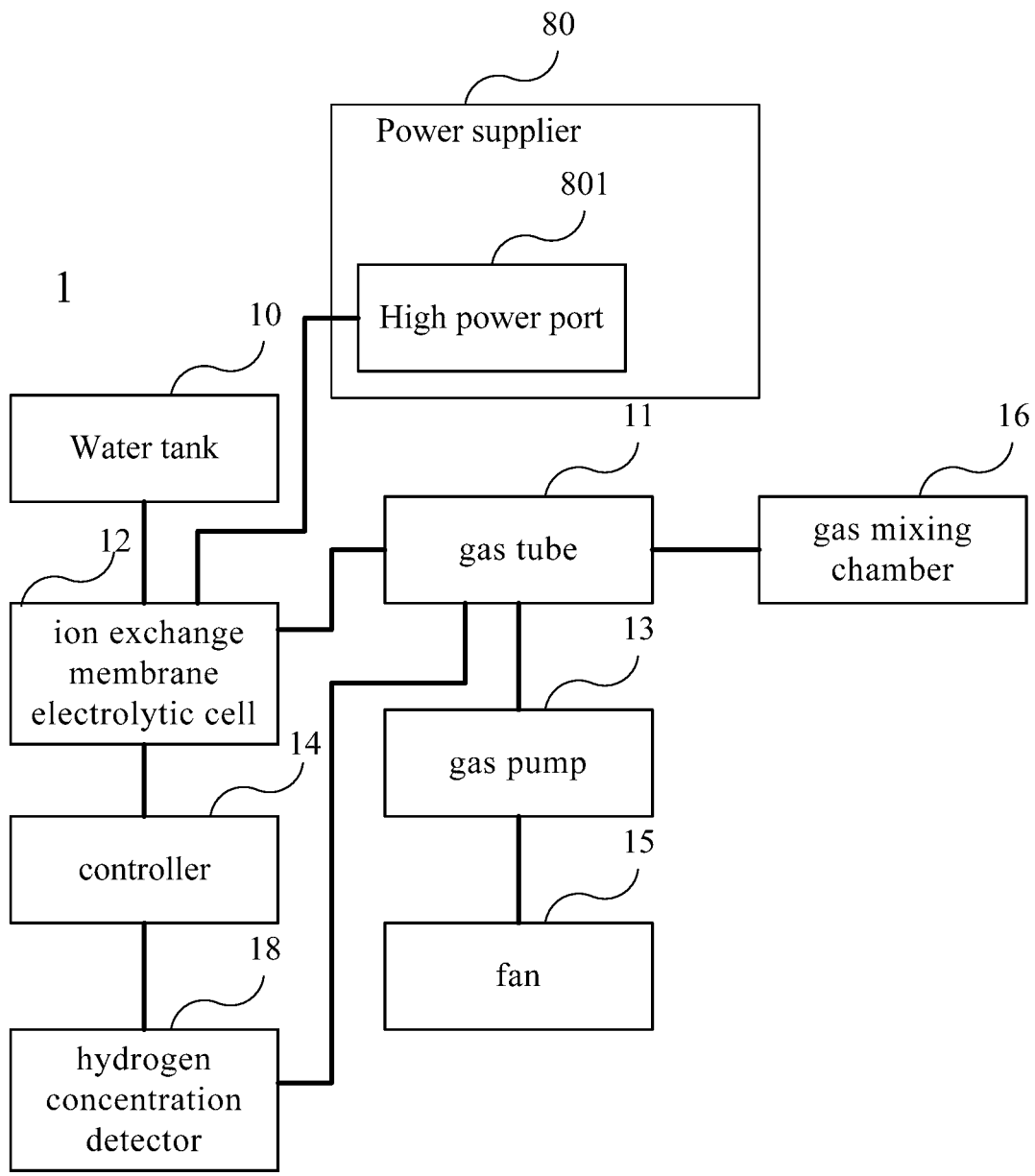
FIG. 1C shows a functional block diagram of one embodiment of the electrolysis device in the present invention.

Please refer to FIG. 1A to FIG. 1C. FIG. 1A shows an appearance view of one embodiment of the electrolysis device in the present invention. FIG. 1B shows an appearance view of the electrolysis device without the shell of FIG. 1A in the present invention. FIG. 1C shows a functional block diagram of one embodiment of the electrolysis device in the present invention. The electrolysis device in the present invention comprises a housing 100 and an operation panel 102. The housing 100 comprises a side wall and a base. A water tank 10 and an ion exchange membrane electrolytic cell 12 are configured within the housing 100. The water tank 10 is configured at a side opposite to the operation panel 102. The water tank 10 is configured for providing water to the ion exchange membrane electrolytic cell 12. The ion exchange membrane electrolytic cell 12 is configured between the operation panel 102 and the water tank 10, and the ion exchange membrane electrolytic cell 12 is located at a non-center within the housing. The ion exchange membrane electrolytic cell 12 electrolyzes water to generate hydrogen. In an embodiment, the water is deionized water for preparing hydrogen with high purity. However, it is not limited to deionized water.

Figures 2A, 2B:
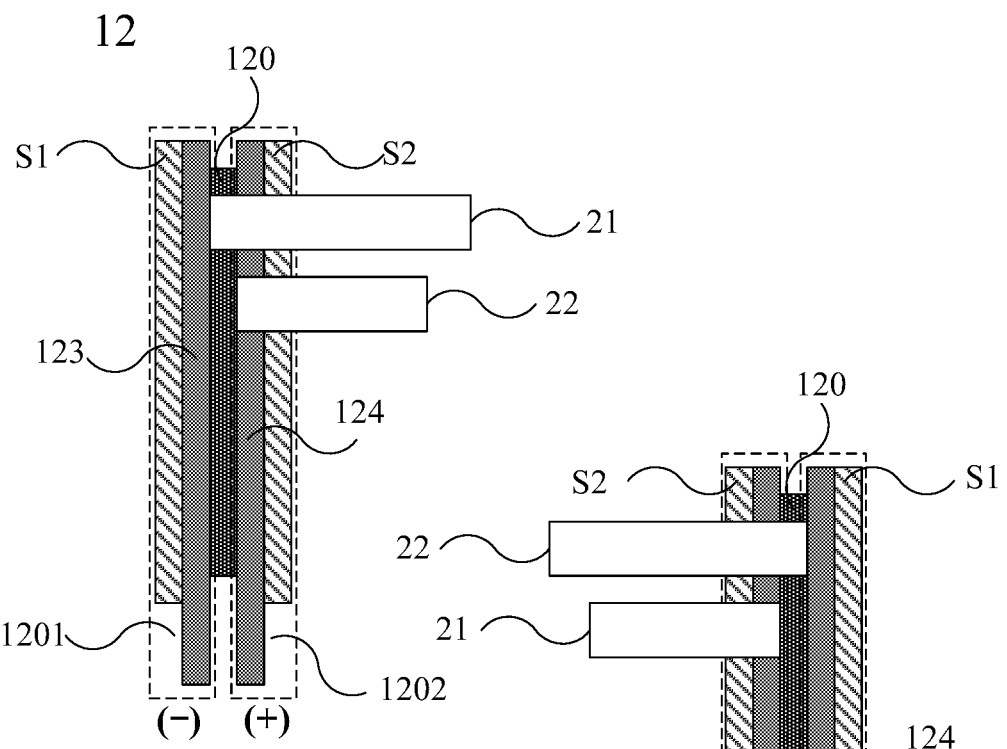
FIG. 2A shows a sectional schematic diagram of one embodiment of the ion exchange membrane electrolytic cell in the present invention.
FIG. 2B shows a sectional schematic diagram of another embodiment of the ion exchange membrane electrolytic cell in the present invention.

Please refer to FIG. 2A and FIG. 2B. FIG. 2A shows a sectional schematic diagram of one embodiment of the ion exchange membrane electrolytic cell in the present invention. FIG. 2B shows a sectional schematic diagram of another embodiment of the ion exchange membrane electrolytic cell in the present invention. FIG. 2A and FIG. 2B will be used to briefly illustrate the main features of the present invention in this section. Please refer to FIG. 2A. The ion exchange membrane electrolytic cell 12 comprises a first side S1, a second side S2 corresponding to the first side S1, an ion exchange membrane 120, a cathode 123, an anode 124, a hydrogen output tube 21, and an oxygen output tube 22. The ion exchange membrane 120 is configured between the first side S1 and the second side S2. The cathode 123 is configured between the first side S1 and the ion exchange membrane 120. The anode 124 is configured between the second side S2 and the ion exchange membrane 120. Wherein, the area having the first side S1 and the cathode 123 is called as the cathode chamber 1201. The area having the second side S2 and the anode 124 is called as the anode chamber 1202. However, in order to more clearly express the corresponding positions of the cathode chamber 1201 and the anode chamber 1202, the position of the cathode chamber 1201 and the anode chamber 1202 is indicated by a dashed line in FIG. 2A. The hydrogen output tube 21 extends from the area between the ion exchange membrane 120 and the first side S1 to the second side S2, and penetrates through the second side S2. The oxygen output tube 22 extends from the area between the ion exchange membrane 120 and the second side S2 to the second side S2, and penetrates through the second side S2. While the ion exchange membrane electrolytic cell 12 electrolyzes water, the cathode 123 generates hydrogen and the anode 124 generates oxygen. The main features of the present invention is that the hydrogen and the oxygen are respectively outputted via the hydrogen output tube 21 and the oxygen output tube 22 from the second side S2 of the ion exchange membrane electrolytic cell 12. In the present embodiment, the hydrogen output tube 21 and the oxygen output tube 22 output the hydrogen and the oxygen from the side near the anode chamber 1202 of the ion exchange membrane electrolytic cell 12.

However, the position of the hydrogen output tube 21 and the oxygen output tube 22 in the present invention is not limited to the described embodiment. Please refer to FIG. 2B. The components of the ion exchange membrane electrolytic cell 12 shown in FIG. 2B are the same as those of FIG. 2A. The difference is that the position of the first side S1 and the second side S2 in FIG. 2B is opposite to that in FIG. 2A. Therefore, in FIG. 2B, the anode 124 is configured between the first side S1 and the ion exchange membrane 120. The cathode 123 is configured between the second side S2 and the ion exchange membrane 120. The anode chamber 1202 has the first side S1 and the anode 124. The cathode chamber 1201 has the second side S2 and the cathode 123. The hydrogen output tube 21 extends from the area between the ion exchange membrane 120 and the second side S2 to the second side S2, and penetrates through the second side S2. The oxygen output tube 22 extends from the area between the ion exchange membrane 120 and the first side S1 to the second side S2, and penetrates through the second side S2. While the ion exchange membrane electrolytic cell 12 electrolyzes water, the cathode 123 generates hydrogen and the anode 124 generates oxygen. The main features of the present invention is that the hydrogen and the oxygen are respectively outputted via the hydrogen output tube 21 and the oxygen output tube 22 from the second side S2 of the ion exchange membrane electrolytic cell 12. In the present embodiment, the hydrogen output tube 21 and the oxygen output tube 22 output the hydrogen and the oxygen from the side near the cathode chamber 1201 of the ion exchange membrane electrolytic cell 12. This also indicates that the hydrogen output tube 21 and the oxygen output tube 22 could be configured at any side of the ion exchange membrane electrolytic cell 12 according to the design or the demand of the users.

Figure 2C:
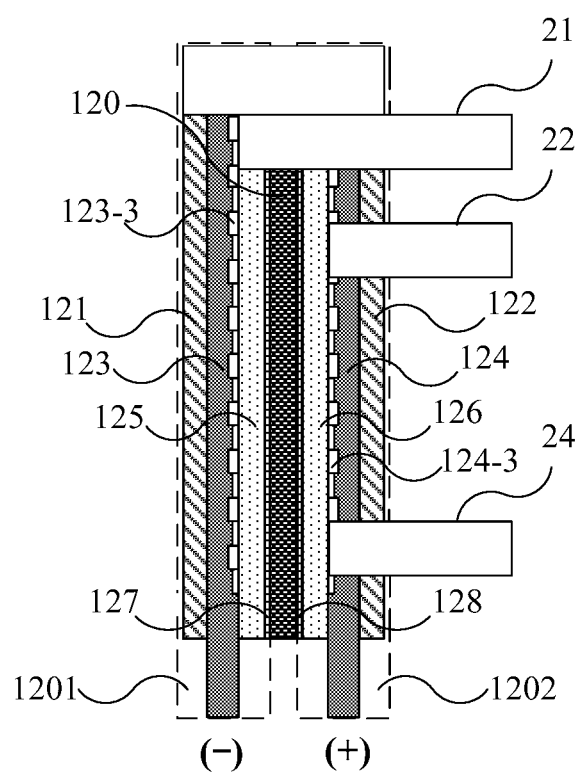
FIG. 2C shows a sectional schematic diagram of one embodiment according to FIG. 2A in the present invention.

Please refer to FIG. 2C. FIG. 2C shows a sectional schematic diagram of one embodiment according to FIG. 2A in the present invention. The ion exchange membrane electrolytic cell 12 comprises the ion exchange membrane 120, the cathode chamber 1201, and the anode chamber 1202, as shown in FIG. 2C. The cathode chamber 1201 accommodates the cathode 123, and the anode chamber 1202 accommodates the anode 124. The ion exchange membrane electrolytic cell 12 is configured between the cathode chamber 1201 and the anode chamber 1202. While the ion exchange membrane electrolytic cell 12 electrolyzes water, the cathode 123 generates hydrogen and the anode 124 generates oxygen. In an embodiment, the anode chamber 1202 accommodates water. The water in the anode chamber 1202 may further penetrate into the cathode chamber 1201 through the ion membrane 120. Besides, FIG. 2A, FIG. 2B, and FIG. 2C are the sectional schematic diagrams for demonstrating the structure inside the ion exchange membrane electrolytic cell 12, but not to disclose the actual ion exchange membrane electrolytic cell 12. The blank area in FIG. 2C shows the housing of the ion exchange membrane electrolytic cell 12.

The ion exchange membrane 120 comprises an ion exchange membrane body 1203, the anode catalyst layer 128 and the cathode catalyst layer 127, as shown in FIG. 2C. The ion exchange membrane body 1203 can be a proton exchange membrane. In a better embodiment, the ion exchange membrane body is a Nafion membrane. The anode catalyst layer 128 can be selected from a group consisting of Pt, Ir, Pd, the alloy powder of Pt, carbon or any combination of thereof. The cathode catalyst layer 127 can be selected from a group consisting of Pt, Ir, Pd, the alloy powder of Pt, or any combination of thereof. In an embodiment, the material of the anode catalyst layer 128 or the cathode catalyst layer 127 is able to be slurry which is disposed on two sides of the ion membrane to form the anode catalyst layer 128 and the cathode catalyst layer 127. In practice, the hydrogen may be generated by the catalyst layer, and hydrogen may be generated by the cathode 123 instead; hydrogen may be even generated between the ion exchange membrane body 1203 and the cathode 123. Therefore, compare to the prior art, the ion exchange membrane electrolytic cell 12 in the present invention may avoid several problems such as cell corrosion, environmental pollution, or inhalation with electrolyte gas due to incomplete filtration.

Please refer to FIG. 2A to FIG. 2C. Inside the cathode chamber 1201 comprises a cathode platen 121, the cathode 123, a cathode seal plate 125, and the cathode catalyst layer 127. Inside the anode chamber 1202 comprises an anode platen 122, the anode 124, an anode seal plate 126, and the anode catalyst layer 128. Wherein, the first side S1 and the second side S2 in FIG. 2A is respectively corresponding to the cathode platen 121 and the anode platen 122 in FIG. 2C. On the other hand, the first side S1 and the second side S2 in FIG. 2B are corresponding to the anode platen 122 and the cathode platen 121 in FIG. 2C respectively. The ion exchange membrane electrolytic cell 12 comprises the hydrogen output tube 21, the oxygen output tube 22, and a water tube 24. The oxygen output tube 22 is configured for outputting the oxygen, and the hydrogen output tube 21 is configured for outputting the hydrogen generated within the cathode chamber 1201. The hydrogen output tube 21 penetrates through the cathode seal plate 125, the anode seal plate 126, the anode 124, and the anode platen 122, as shown in FIG. 2C. Therefore, the cathode chamber 1201 could be connected to the environment outside the ion exchange membrane electrolytic cell 12 and output the hydrogen. The oxygen output tube 22 is configured for outputting the oxygen generated within the anode chamber 1202. The oxygen output tube 22 penetrates through the anode 124 and the anode platen 122, so that the anode chamber 1202 could be connected to the environment outside the ion exchange membrane electrolytic cell 12 and output the oxygen. The water tube 24 penetrates through the anode 124 and the anode platen 122. The water tube 24 is connected to the water tank 10 for introducing the water in the water tank 10 into the anode chamber 1202. Therefore the water for electrolyzing in the ion exchange membrane electrolytic cell 12 is replenished. Wherein, since the hydrogen output tube 21 and the oxygen output tube 22 are configured at the same side of the ion exchange membrane electrolytic cell 12, the oxygen and the hydrogen are outputted at the same side of the ion exchange membrane electrolytic cell 12. In the present embodiment, all of the hydrogen output tube 21, the oxygen output tube 22, and the water tube 24 penetrate through the anode platen 122, and are configured at the anode platen 122. The present invention is not limit to the described embodiment. With a similar structure, the hydrogen output tube 21, the oxygen output tube 22, and the water tube 24 may also penetrate through and be disposed on the cathode platen 121, as shown as the second side S2 in FIG. 2B.

In prior art, since the gas and the water are outputted from two, even three sides of the ion exchange membrane electrolytic cell, a large accommodating space for ion exchange membrane electrolytic cell and the connective line and connective tube must be reserved. In the present invention, since the oxygen and the hydrogen are outputted at the same side of the ion exchange membrane electrolytic cell 12, the space around the ion exchange membrane electrolytic cell can be used effectively.

Figure 3:
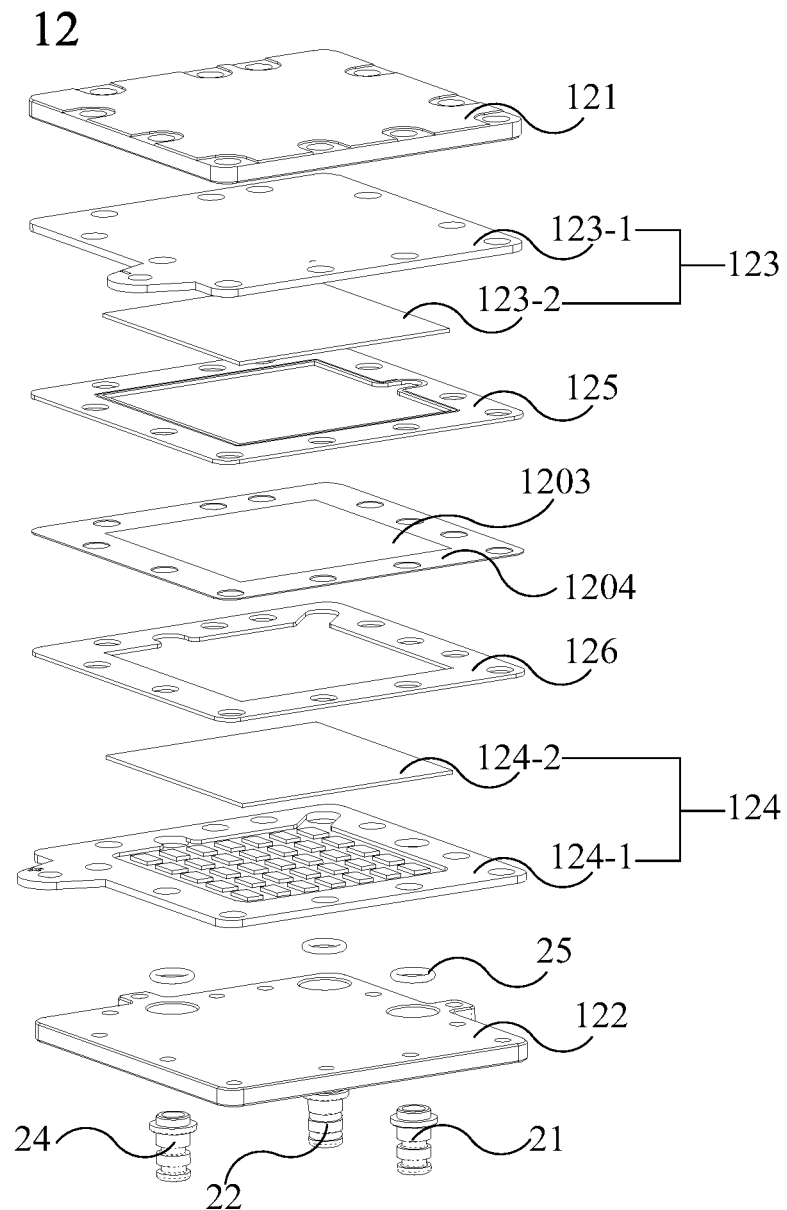
FIG. 3 shows an exploded diagram of one embodiment of the ion exchange membrane electrolytic cell in the present invention.
Figure 4:
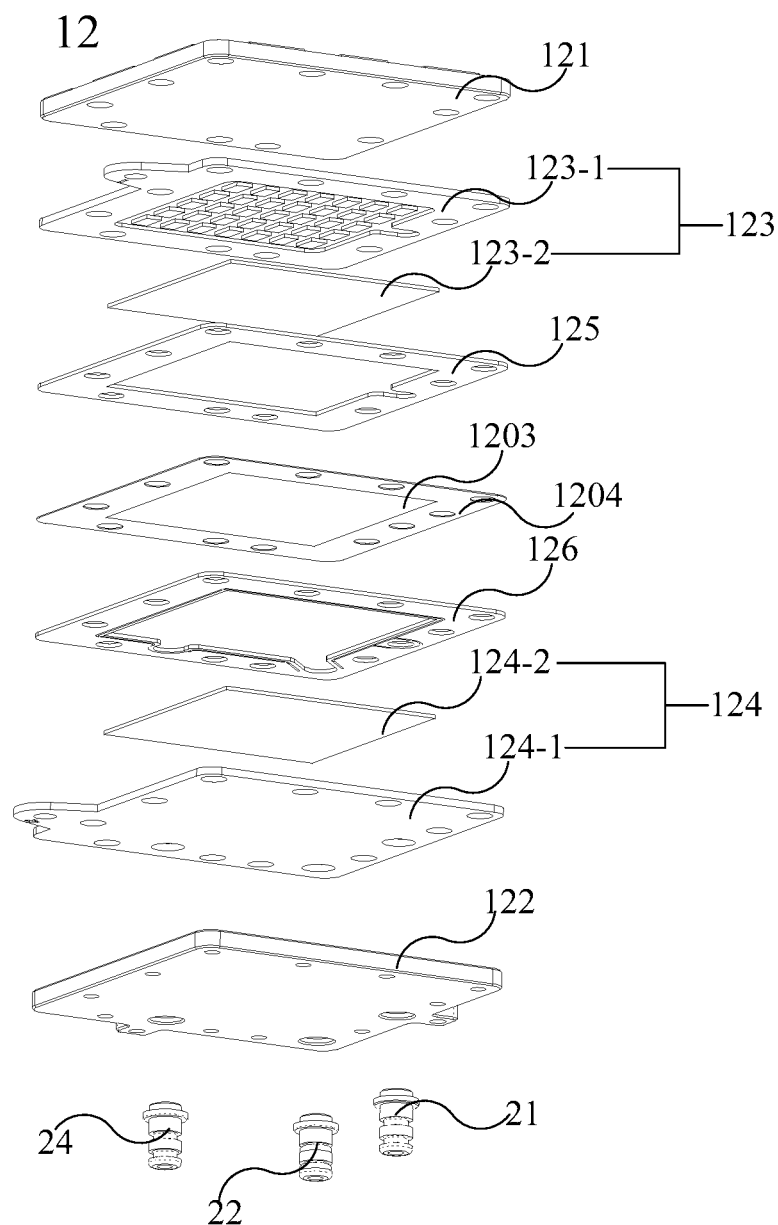
FIG. 4 shows another exploded diagram of FIG. 3 of the ion exchange membrane electrolytic cell in the present invention.

Please refer to FIG. 3 and FIG. 4. FIG. 3 shows an exploded diagram of one embodiment of the ion exchange membrane electrolytic cell in the present invention. FIG. 4 shows another exploded diagram of FIG. 3 of the ion exchange membrane electrolytic cell in the present invention. The ion exchange membrane 120 further comprises an ion exchange membrane peripheral plate 1204 for fixing the relatively position of the ion exchange membrane body 1203, the cathode catalyst layer 127, and the anode catalyst layer 128 in the ion exchange membrane electrolytic cell 12. FIG. 3 and FIG. 4 show the relative position of each component of the ion exchange membrane electrolytic cell 12. Then each component contained by the ion exchange membrane electrolytic cell 12 can be assembled according to the stacking sequence as shown in FIG. 3 and FIG. 4.

Please refer to FIG. 3 and FIG. 4. In an embodiment, the ion exchange membrane peripheral plate 1204, the cathode seal plate 125, and the anode seal plate 126 can configured around the electrode plate to get the effects such as insulation and airtight. Wherein, the material of the ion exchange membrane peripheral plate 1204 can be silicone gel. However, the material and setting method of the ion exchange membrane peripheral plate 1204 is not limited to those mentioned above. In practice, the material and setting method of the ion exchange membrane peripheral plate 1204 can be any kinds of material or setting methods which can get the effects like insulation and airtight.

As shown in FIG. 3 and FIG. 4, the hydrogen output tube 21 penetrates through the cathode seal plate 125, the ion exchange membrane peripheral plate 1204, the anode seal plate 126, the anode 124, and the anode platen 122, so that the hydrogen generated within the cathode chamber 1201 can be outputted via the hydrogen output tube 21 and the ion exchange membrane peripheral plate 1204 from the side of the anode platen 122; and the oxygen output tube 22 penetrates through the anode 124 and the anode platen 122, so that the oxygen generated within the anode chamber 1202 can be outputted via the oxygen output tube 22 from the side of the anode platen 122. The water tube 24 penetrates through the anode 124 and the anode platen 122. The water tube 24 is connected to the water tank 10 for introducing the water in the water tank 10 into the anode chamber 1202. Therefore the water for electrolyzing in the ion exchange membrane electrolytic cell 12 is replenished. A gasket 25 is configured among the hydrogen output tube 21, the oxygen output tube 22, the water tube 24, and the anode platen 122. The gasket 25 is configured for sealing the space among the hydrogen output tube 21, the oxygen output tube 22, the water tube 24, and the anode platen 122.

As shown in FIG. 3 and FIG. 4, the cathode 123 comprises a cathode conductive plate 123-1 and a cathode conductive plate 123-2; the anode 124 comprises an anode conductive plate 124-1 and an anode conductive plate 124-2. In an embodiment, each conductive plate can be a titanium powder casting piece, and the material of each conductive plate may be titanium. However, in practice, it is not limited to the above materials or molding methods. As shown in FIG. 3, in an embodiment, the cathode conductive plate 123-2 can be configured between the ion exchange membrane 120/the ion exchange membrane body 1203 and the cathode conductive plate 123-1; and the anode conductive plate 124-2 can be configured between the ion exchange membrane 120/the ion exchange membrane body 1203 and the anode conductive plate 124-1. The ion exchange membrane electrolytic cell 12 may be connected with a power supplier by the cathode conductive plate 123-1 and the anode conductive plate 124-1. In an embodiment, there are pathways designed in the anode conductive plate 124-1 shown in FIG. 3 and in the cathode conductive plate 123-1 shown in FIG. 4, respectively. While the cathode conductive plate 123-1 and the cathode conductive plate 123-2 are overlapped, a plurality of the cathode cavities 123-3 is formed in the cathode chamber 1201. While the anode conductive plate 124-1 and the anode conductive plate 124-2 are overlapped, a plurality of the anode cavities 124-3 is formed in the anode chamber 1202. The cathode cavities 123-3 and the anode cavities 124-3 can be used for circulating the air and the water therein. Wherein, the anode cavities 124-3 is connected to the oxygen output tube 22 and the cathode cavities 123-3 is connected to the hydrogen output tube 21.

Figure 5A:
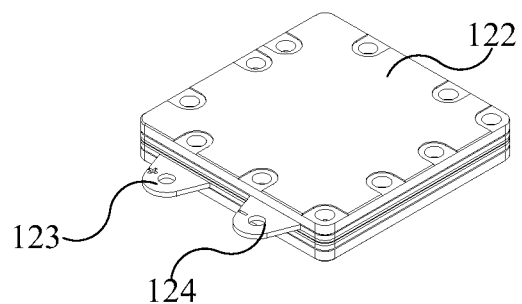
FIGS. 5A and 5B show composition diagrams with different visual angles of the ion exchange membrane electrolytic cell in the present invention.
Figure 5B:
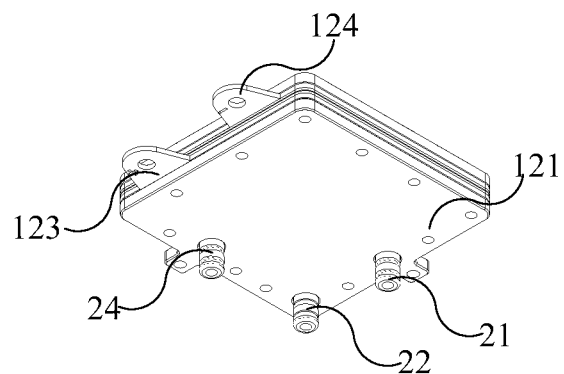
Figure 6:
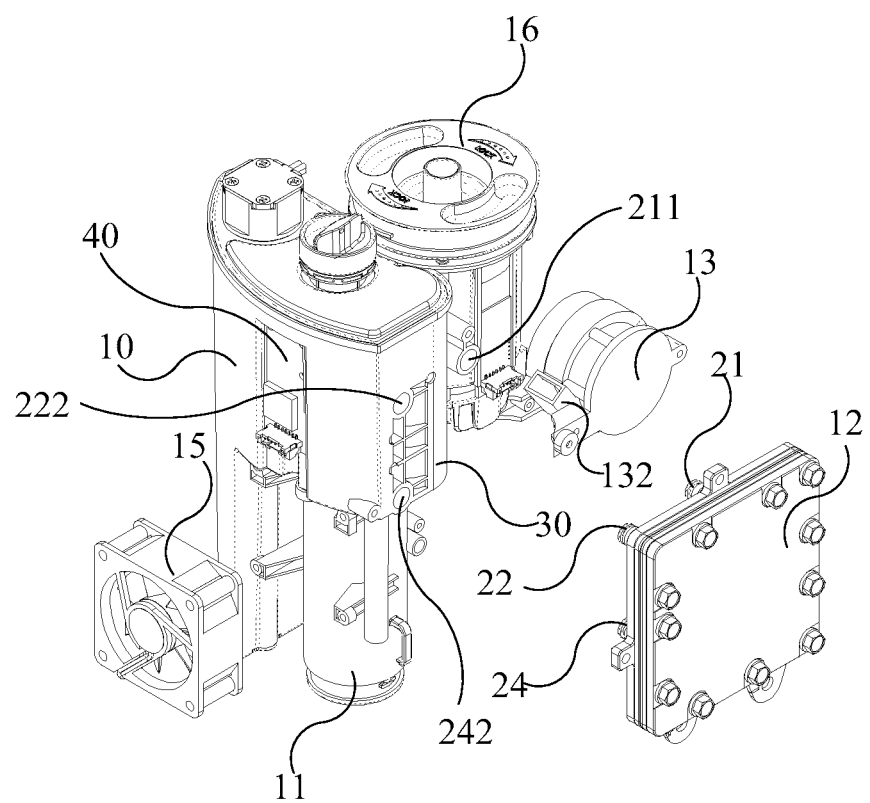
FIG. 6 shows an exploded diagram of one embodiment of the electrolysis device in the present invention.

Please refer to the FIG. 5A and FIG. 5B. FIGS. 5A and 5B show composition diagrams with different visual angles of the ion exchange membrane electrolytic cell in the present invention. The cathode platen 121 and the anode platen 122 respectively disposed at the two outer sides of the ion exchange membrane electrolytic cell 12 for fixing, isolating, and protecting the whole ion exchange membrane electrolytic cell 12. The material of the cathode platen 121 and the anode platen 122 may be stainless steel. In an embodiment, after the ion exchange membrane electrolytic cell 12 is assembled, the ion exchange membrane electrolytic cell 12 can be fixed by the fixing element shown in FIG. 6. However, the quantity, type and fixing manner are not limited to the figure. As shown in FIG. 6, the volume of the assembled ion exchange membrane electrolytic cell 12 is relatively small. Therefore, the volume of the electrolysis device in the present invention is compact.

Figure 7A:
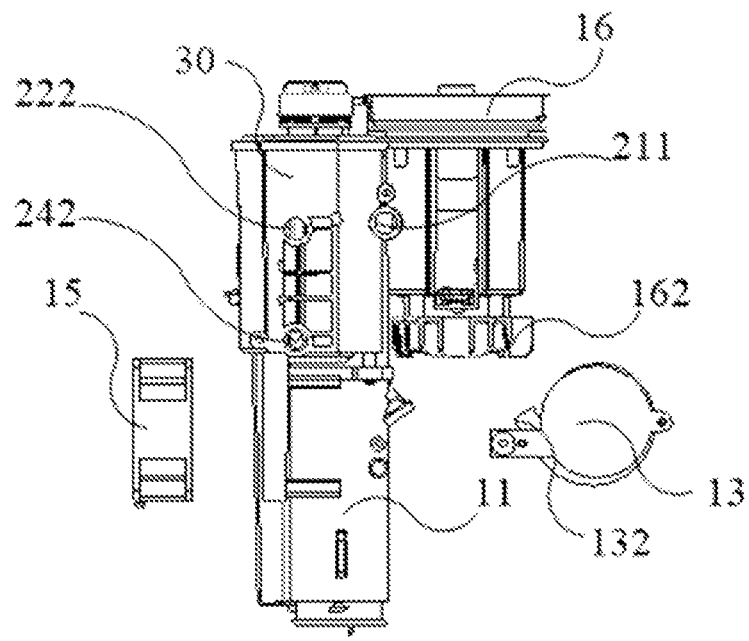
FIGS. 7A and 7B show an exploded diagram and a composition diagram in another visual angle of the electrolysis device in the present invention.
Figure 7B:
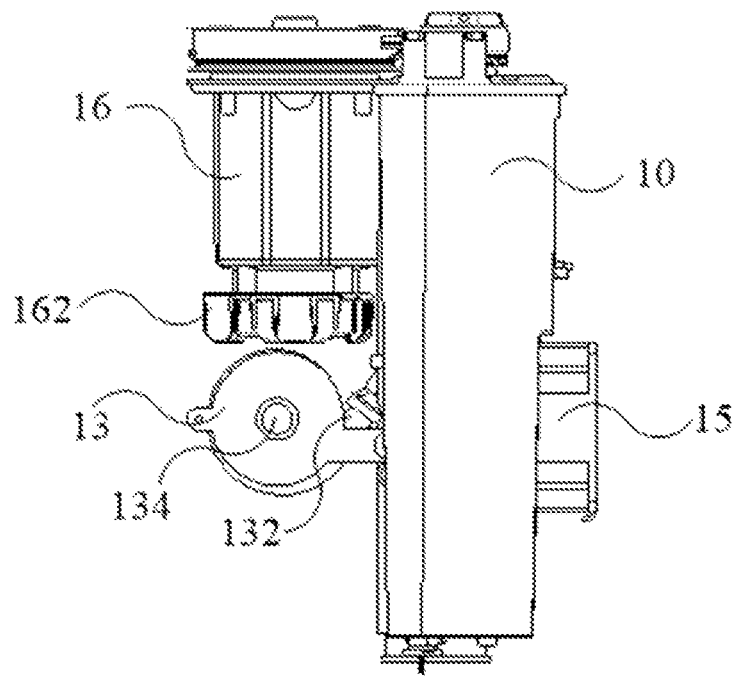

Please refer to the FIG. 1C, FIG. 6, FIG. 7A and FIG. 7B. FIG. 6 shows an exploded diagram of one embodiment of the electrolysis device in the present invention. FIGS. 7A and 7B show an exploded diagram and a composition diagram in another visual angle of the electrolysis device in the present invention. Only the necessary components are shown for illustrating clearly. The electrolysis device 1 of the present invention comprises the water tank 10 and the ion exchange membrane electrolytic cell 12 mentioned above; besides, the electrolysis device 1 also comprises a gas tube 11, a gas pump 13, a fan 15, a gas mixing chamber 16, a hydrogen concentration detector 18, a controller 14, a separation tank 30, and a water gauge 40. The separation tank 30 is located at a isolated room in the water tank 10. In an embodiment, the water gauge 40 is for detecting water level of the water tank 10. The water gauge 40 is configured at the outer surface of the water tank 10 and is used to measures the water volume in the water tank 10 by measuring the difference in capacitance between water area and waterless area in the water tank 10.

Figures 8A, 8B:
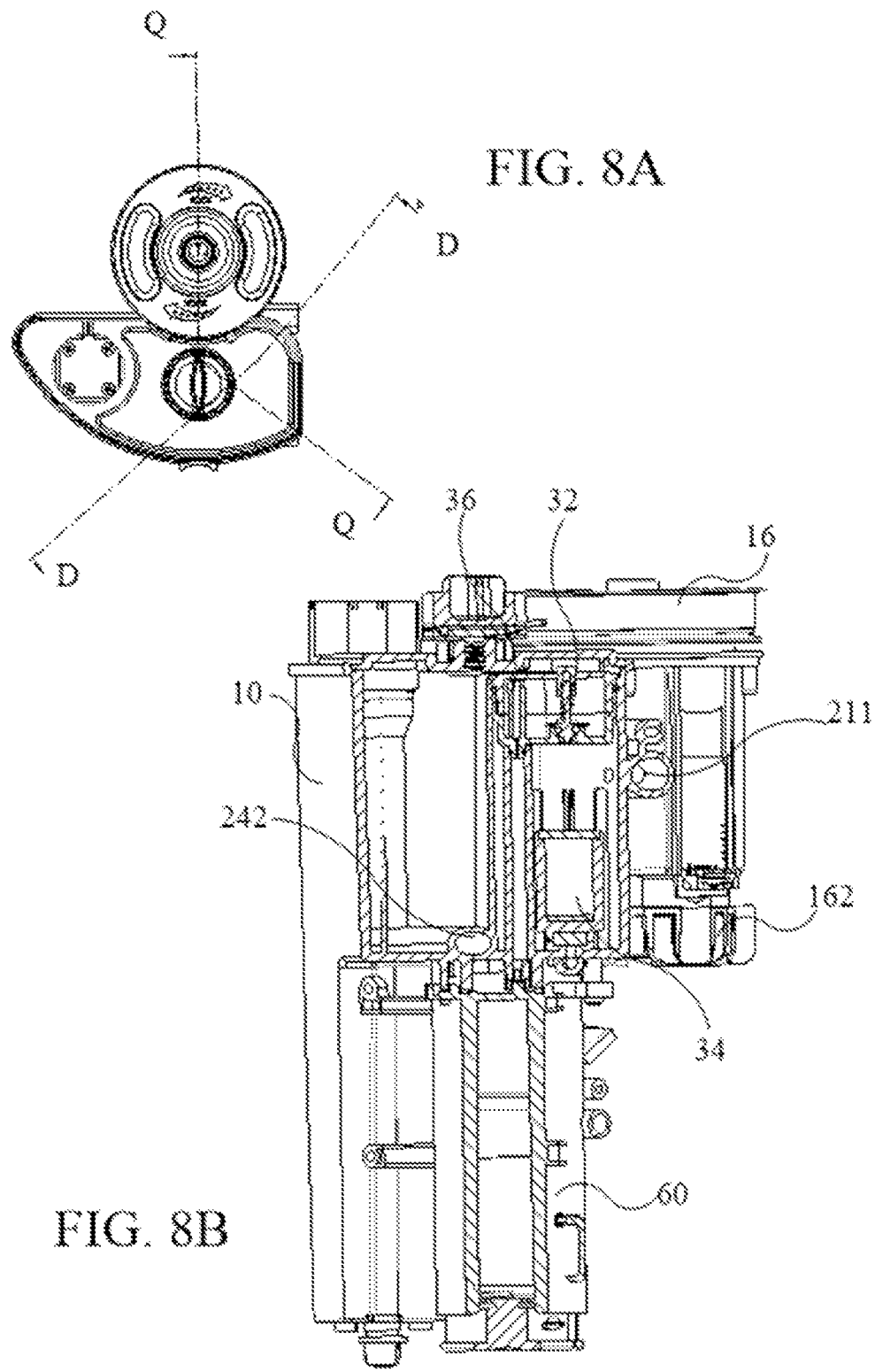
FIG. 8A shows a top view of one embodiment of the electrolysis device in the present invention.
FIG. 8B shows a sectional schematic diagram according to segment D-D of FIG. 8A in the present invention.

Please refer to FIG. 6, FIG. 8A and FIG. 8B. FIG. 8A shows a top view of one embodiment of the electrolysis device in the present invention. FIG. 8B shows a sectional schematic diagram according to segment D-D of FIG. 8A in the present invention. The hydrogen output tube 21 of the ion exchange membrane electrolytic cell 12 is coupled and connected to the separation tank 30 by a hydrogen port 211. The oxygen output tube 22 of the ion exchange membrane electrolytic cell 12 is coupled and connected to the water tank 10 by an oxygen port 222. Wherein, a sterilizer is contained in the water tank 10. In the present embodiment, the sterilizer is a straight UV sterilizer. The sterilizer is located at the side in the water tank 10 away from the separation tank 30. The water tube 24 is connected directly to the side in the water tank 10 near the sterilizer by a water port 242, so that the sterilized water in the water tank 10 is replenished to the ion exchange membrane electrolytic cell 12 for electrolyzing.

The separation tank 30 comprises a spring valve 32, a float 34, and a hydrogen discharge tube 36 therein. The hydrogen generated by the ion exchange membrane electrolytic cell 12 is transported to the separation tank 30 via the hydrogen output tube 21 and the hydrogen port 211. While the hydrogen in the separation tank 30 accumulates to a threshold, the spring valve 32 is opened due to the hydrogen pressure. Therefore, the hydrogen may be outputted via the hydrogen discharge tube 36 to a filter 60. The filter 60 will filter impurities in hydrogen. Besides, when the hydrogen is outputted from the ion exchange membrane electrolytic cell 12, the hydrogen may contain a little residual electrolytic water. The residual electrolytic water is accumulated in the separation tank 30, so that the float 34 floats up with rising water level. Then a water outlet covered by the float 34 is exposed, and the accumulated residual electrolytic water is discharged via the water outlet to the water tank 10 for reusing.

The oxygen generated by electrolyzing is discharged directly to the water tank 10 via the oxygen port 222 and the oxygen output tube 22. The oxygen is directly dissipated from the upper part of the water tank 10 to the atmosphere. The oxygen outputted from the ion exchange membrane electrolytic cell 12 may contain a little residual electrolytic water. The residual electrolytic water will be discharged to the water tank 10 for reusing.

Figure 9:
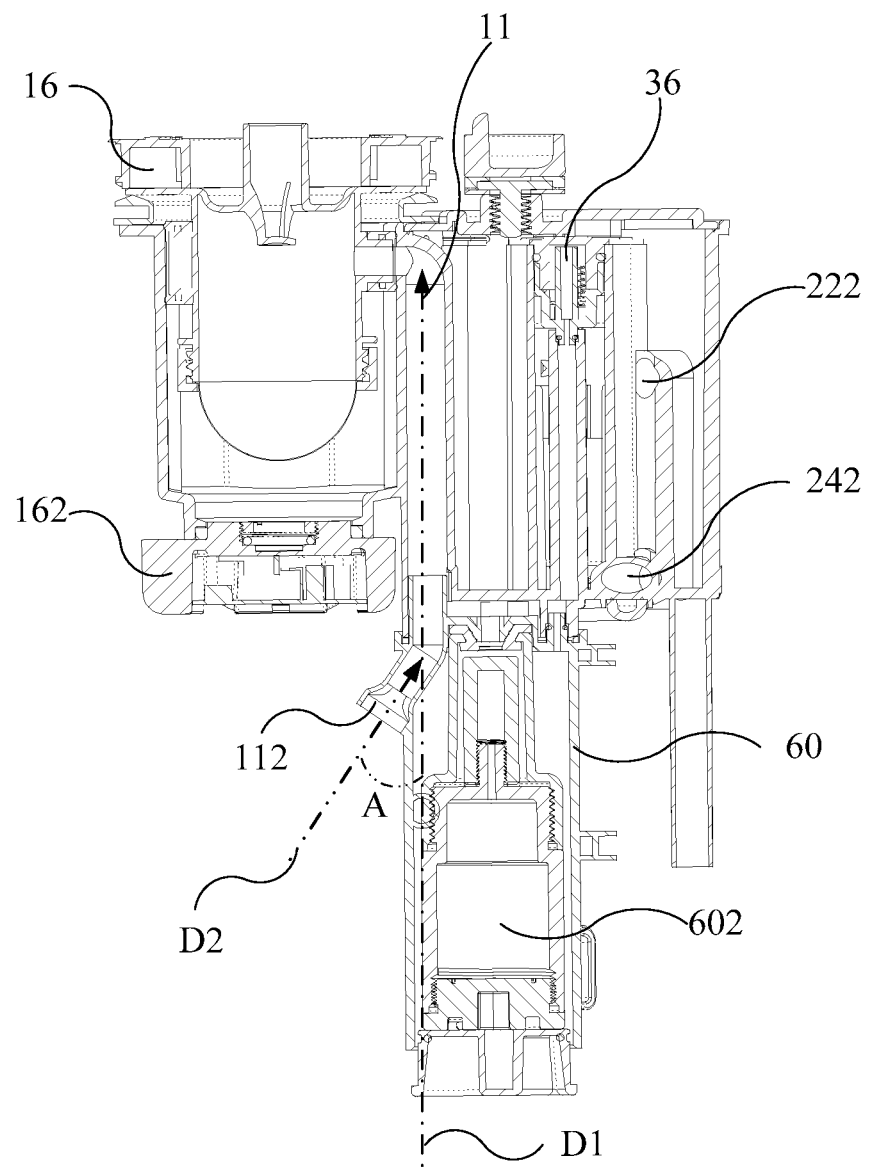
FIG. 9 shows a sectional schematic diagram according to segment Q-Q of FIG. 8A in the present invention.

Please refer to FIG. 7A, FIG. 7B, FIG. 8A, and FIG. 9. FIG. 9 shows a sectional schematic diagram according to segment Q-Q of FIG. 8A in the present invention. As mentioned in previous paragraph, the hydrogen is outputted to the filter 60 via the hydrogen discharge tube 36, then a filter cartridge 602 contained in the filter 60 is used to filter the impurities in hydrogen. The filtered hydrogen is transported to the gas tube 11 and is diluted to enter the gas mixing chamber 16. The gas tube 11 is connected to the filter 60 to receive the filtered hydrogen. The gas tube 11 is also connected to the gas pump 13. The fan 15 draws the air from external environment out of the electrolysis device 1 into the electrolysis device 1, and the gas pump 13 draws the air into the gas tube 11 for diluting the hydrogen concentration inside the gas tube 11. Wherein, all of the components mentioned above are encased in the housing 100. The housing 100 has a plurality of pores. The fan 15 draws the environment air into the electrolysis device 1 by the pores on the housing 100, and then the drawn air is drawn into the gas tube 11 by the gas pump 13. In the present invention, the gas pump 13 may be a vortex fan. The air drawn by the fan 15 is drawn into the gas pump 13 via a suction port 134 of the gas pump 13, so that the air can be transported to the gas tube 11. As shown in FIG. 7B and FIG. 9, a gas pump tube 132 of the gas pump 13 is coupled to the gas tube 11 via a gas inlet 112. The gas tube 11 has a first flowing direction D1, and the gas inlet 112 has a second flowing direction D2. The gas in the gas tube 11 flows to the gas mixing chamber 16 in the first flowing direction D1, shown as the arrow on the indicating line. The gas in the gas inlet 112 flows into the gas tube 11 in the second flowing direction D2, shown as the arrow on the indicating line. So that the gas from the gas pump tube 132 is inputted to the gas tube 11 via the gas inlet 112. A linking position between the gas inlet 112 and the gas tube 11, which is the intersection of the first flowing direction D1 and the second flowing direction D2, is provided with an angle A. The angle A is less than 90 degrees. The preferred angle of the angle A is in a range between 25 degrees and 45 degrees. The shape of the linking position with the angle A is made into an arc angle. By the design of the angle A, the air in the gas pump tube 132 can be transported into the gas tube 11 to dilute the hydrogen in the gas tube 11.

Please refer to FIG. 9. The gas mixing chamber 16 is connected to the gas tube 11 and receives the filtered and diluted hydrogen. The gas mixing chamber 16 selectively generates an atomized gas for mixing with the hydrogen to form a healthy gas, and the atomized gas is the one selected from a group consisting of water vapor, atomized solution, volatile essential oil, and any combination thereof. The gas mixing chamber 16 comprises a shaker 162. The shaker 162 atomizes the water vapor, the atomized solution, or the volatile essential oil in the gas mixing chamber 16 by shaking to generate the atomized gas. Then the atomized gas is mixed with hydrogen in the gas mixing chamber 16 to form the healthy gas for inhaling. The gas mixing chamber 16 may selectively turn on or turn off according to the requirement. That also means the gas mixing chamber 16 and the shaker 162 can be turned on to provide the hydrogen with the atomized gas for inhaling; otherwise, the gas mixing chamber 16 and the shaker 162 can be turned off to provide the hydrogen only for inhaling. The user may inhale the hydrogen or the healthy gas by releasing the hydrogen or the healthy gas into the atmosphere. Also, the user may inhale the hydrogen or the healthy gas via a pipe or a mask.

The hydrogen concentration detector 18 is connected to the gas tube 11 for detecting the hydrogen concentration of the gas tube 11. The controller 14 is coupled to the hydrogen concentration detector 18, the gas pump 13 and the ion exchange membrane electrolytic cell 12. In an embodiment, the hydrogen concentration detector 18 may be coupled to the hydrogen output tube 21 and the hydrogen port 211 for detecting the hydrogen concentration of the gas tube 11 outputted from the ion exchange membrane electrolytic cell 12. Wherein, the hydrogen concentration detector 18 detects whether the hydrogen concentration of the gas tube 11 is in a range. The range is between a first threshold and a second threshold. For example, the first threshold is 4% and the second threshold is 6%, then the hydrogen concentration detector 18 detects whether the hydrogen concentration of the gas tube is between 4% and 6%. The value of the first threshold and the second threshold can be adjusted through the operation panel 102 according to the requirement. In the present embodiment, the hydrogen concentration detector 18 generates a first warning signal while the detected hydrogen concentration in the hydrogen output tube 21 and the hydrogen port 211 is higher than the first threshold 4%. The controller 14 generates a start command when receiving the first warning signal. The start command is sent to the gas pump 13 for turning on the gas pump 13. The hydrogen concentration detector 18 generates a second warning signal while the detected hydrogen concentration in the hydrogen output tube 21 and the hydrogen port 211 is higher than the second threshold 6%. The controller 14 generates a stop command when receiving the second warning signal. The stop command is sent to the ion exchange membrane electrolytic cell 12 for turning off the ion exchange membrane electrolytic cell 12. For example, the power inputted to the ion exchange membrane electrolytic cell 12 is cut off to avoid gas explosion due to high hydrogen concentration, further to improve overall safety. The mentioned first threshold can be 3.5% hydrogen volume of the total gas volume. The first warning signal is generated when the detected hydrogen concentration is higher than 3.5%. However, the threshold is not limited to this.

Figure 10:
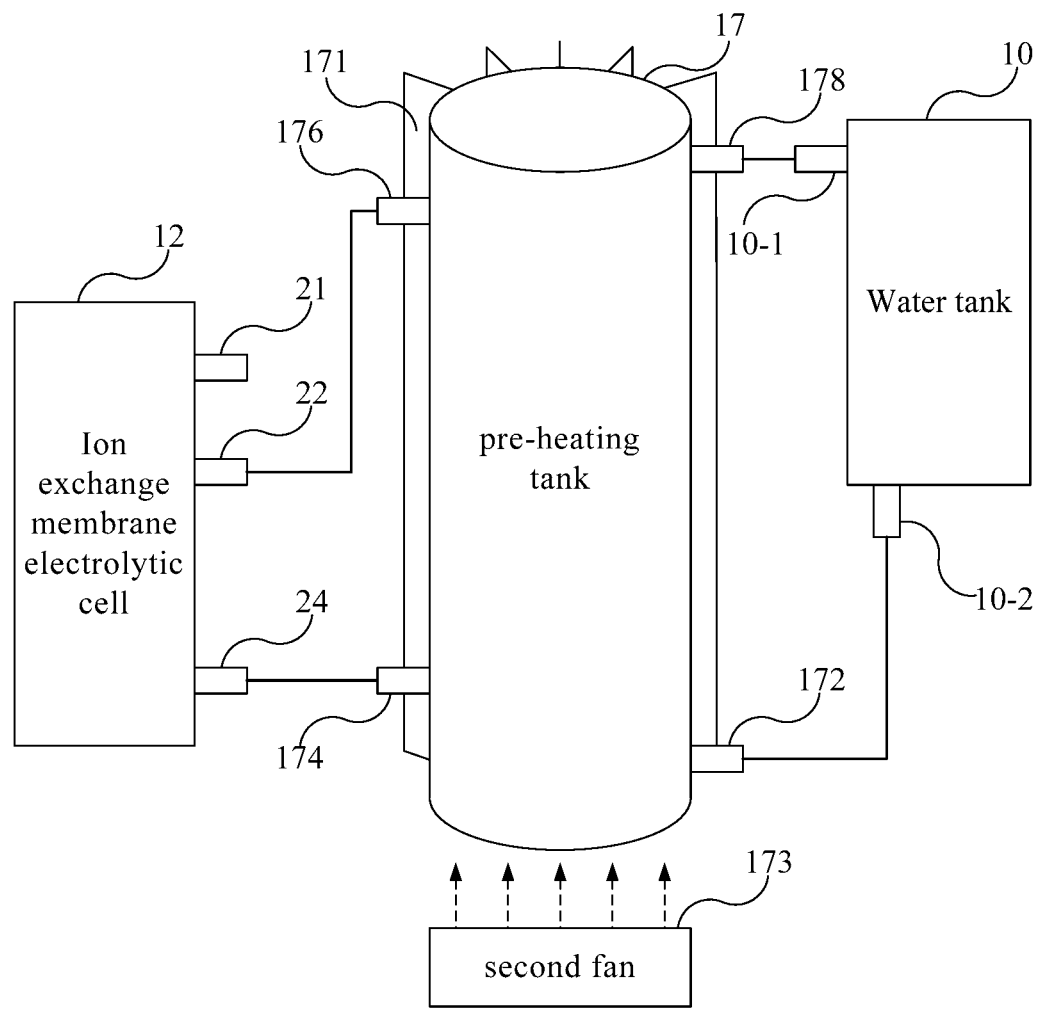
FIG. 10 shows a schematic diagram of one embodiment of the electrolysis device in the present invention.

Please refer to FIG. 10. FIG. 10 shows a schematic diagram of one embodiment of the electrolysis device in the present invention. In an embodiment, the electrolysis device 1 comprises the pre-heating tank 17 configured between the water tank 10 and the ion exchange membrane electrolytic cell 12. Wherein, the pre-heating tank 17 is roughly a cylinder or a circular tube. Although the pre-heating tank 17 is shown larger than the water tank 10 in FIG. 10, the volume of the pre-heating tank 17 is smaller than that of the water tank 10 in other embodiments. The pre-heating tank 17 comprises a water inlet 172 coupled to a bottom port 10-2 of the water tank 10. The pre-heating tank 17 further comprises a water outlet 174 coupled to the water tube 24 of the ion exchange membrane electrolytic cell 12. The pre-heating tank 17 further comprises an oxygen import tube 176 coupled to the oxygen output tube 22. The pre-heating tank 17 further comprises an oxygen export tube 178 coupled to a top port 10-1 of the water tank 10. The water in the water tank 10 flows into the pre-heating tank 17 via the bottom port 10-2 at first, then flows into the ion exchange membrane electrolytic cell 12 for electrolyzing via the water outlet 174. Oxygen and part of the residual electrolyzed water generated during electrolyzing water are discharged into the pre-heating tank 17 via the oxygen import tube 176. Part of the residual electrolyzed water will be remained in the pre-heating tank 17. The oxygen is discharged into the water tank 10 via the top port 10-1 and the oxygen export tube 178.

Wherein, the temperature of the ion exchange membrane electrolytic cell 12 will increase while electrolyzing. The temperature of the electrolyzed water is related to the electrolysis efficiency. The temperature range of electrolyzed water about 55° C. to 65° C. increases the electrolysis efficiency. Therefore, the electrolyzed water in the pre-heating tank 17 is preheated to the appropriate temperature by recovering the electrolyzed water with high temperature discharged by the oxygen output tube 22 of the ion exchange membrane electrolytic cell 12 into the pre-heating tank 17. The appropriate temperature may be in a range between 55° C. to 65° C. In order to maintain the electrolyzed water with appropriate temperature in the pre-heating tank 17, the pre-heating tank 17 further comprises a plurality of cooling fins 171 and a second fan 173. The cooling fins 171 are radially configured on an outside wall of the pre-heating tank 17, and the second fan 173 is configured on an end of the pre-heating tank 17. The cooling fins 171 works with the second fan 173 to generate convection for cooling the pre-heating tank 17. For a simple illustration, the cooling fins 171 are only drawn on a portion of the outer wall of the pre-heating tank 17, and in other embodiments, the cooling fins 171 may be distributed on the outer wall of the pre-heating tank 17. In one embodiment, the water electrolysis device further comprises an integrated water tank module having a water tank configured to supply the water to the ion exchange membrane electrolytic cell, wherein the integrated water tank module receives the hydrogen and the oxygen generated by the ion exchange membrane electrolytic cell through the hydrogen output tube and the oxygen output tube, respectively. In one embodiment, the water electrolysis device further comprises an integrated water tank module having a water tank, a hydrogen port, an oxygen port, and a water port, wherein the hydrogen port, the oxygen port, and the water port are fluidly coupled to the ion exchange membrane electrolytic cell. In one embodiment, the ion exchange membrane electrolytic cell further comprises a casing, the oxygen output tube, the hydrogen output tube and the water tube extend from the casing of the ion exchange membrane electrolytic cell. In one embodiment, the integrated water tank module further comprises a pre-heating tank. In one embodiment, the integrated water tank module further comprises a gas tube, and the water electrolysis device further comprises a gas pump, wherein the gas tube is coupled to hydrogen output tube to receive the hydrogen, and the gas pump draws a gas into the gas tube to dilute the hydrogen inside the gas tube. In one embodiment, the water electrolysis device further comprises an integrated pathway water tank module having a water tank coupled to the ion exchange membrane electrolytic cell to replenish the water to the ion exchange membrane electrolytic cell and a gas pathway, with a hydrogen port and an oxygen port, coupled to the ion exchange membrane electrolytic cell to transport the hydrogen and the oxygen.

An object of the present invention is to reduce the noise and the volume of the electrolysis device 1 while maintaining a sufficient amount of hydrogen production, so that the electrolysis device 1 may be suitable for being used while sleeping. Therefore, the main purpose of the present invention is to reduce the volume of the electrolysis device 1. For example, the electrolysis device 1 of the present invention is roughly cylindrical. Since the longest section length at the bottom is 200 mm and the height of the device is up to 270 mm, the maximum volume is about 8500 cm3, or 8.5 liters. The appearance of the electrolysis device 1 of the present invention is not limited to cylindrical; the appearance of the electrolysis device 1 can be other shape. For example, the appearance of the electrolysis device 1 can be ellipse, square or polygon. Then the accommodation space defined by the housing of the electrolysis device 1 is effectively used as far as possible. There are six outputting setting for adjusting the hydrogen generating rate of the electrolysis device 1, including 120 ml/min, 240 ml/min, or 360 ml/min of hydrogen generating rate respectively corresponding to 2 L/min, 4 L/min, and 6 L/min of total gas (healthy gas). Also, the electrolysis device 1 may output 400 ml/min, 500 ml/min, or 600 ml/min of the hydrogen. The user may adjust the hydrogen generating rate and the type of gas by operation panel. The user can adjust the hydrogen generating rate to decrease the noise while sleeping, so that the present invention can be disposed near the user's head.

Please refer to FIG. 1C again. In an embodiment, the electrolysis device 1 comprises a power supplier 80 for converting the mains to output the 240 watts of direct current to supply electrolysis device 1. The power supplier 80 comprises a high power port 801 and a low power port. The high power port 801 is coupled to the ion exchange membrane electrolytic cell 12 for supplying the power in electrolytic reaction. The low power port is suitable for supplying power to other devices of the electrolytic device 1, such as the gas pump 13, the controller 14, the fan 15, and the hydrogen concentration detector 18. In order to simplify the drawings, only the power supplier 80 and the high power port 801 are depicted in FIG. 1C. However, the person with general knowledge should be able to know how to configure a power line in an electrolysis water device at the low power port for supplying power required for the operation of the electrolysis device 1.

The electric power outputted from the low power port is less than 50% of the electric power outputted from the high power port 801. 172 watts of the 240 watts DC supplied by the power supplier 80 is outputted from high power port 801 to the ion exchange membrane electrolytic cell 12. The high power port 801 outputs a first voltage and a first current. The first voltage is in a range between 3 Volts to 6.3 Volts, and the first current is in a range between 10 amps to 27.3 amps. The low power port supplies 60 watts DC to operate the electrolysis device 1. The low power port outputs a second voltage and a second current. The second voltage may be 24 Volts and the second current is 2.5 amps. In another embodiment, the second voltage may be 5 Volts and the second current is 0.5 amps. It can be known after comparison that the first voltage is less than the second voltage, and the first current is greater than the second current. The high power port 801 outputs a DC with high current and low voltage. The low power port outputs a DC with low current and high voltage.

Figure 11:
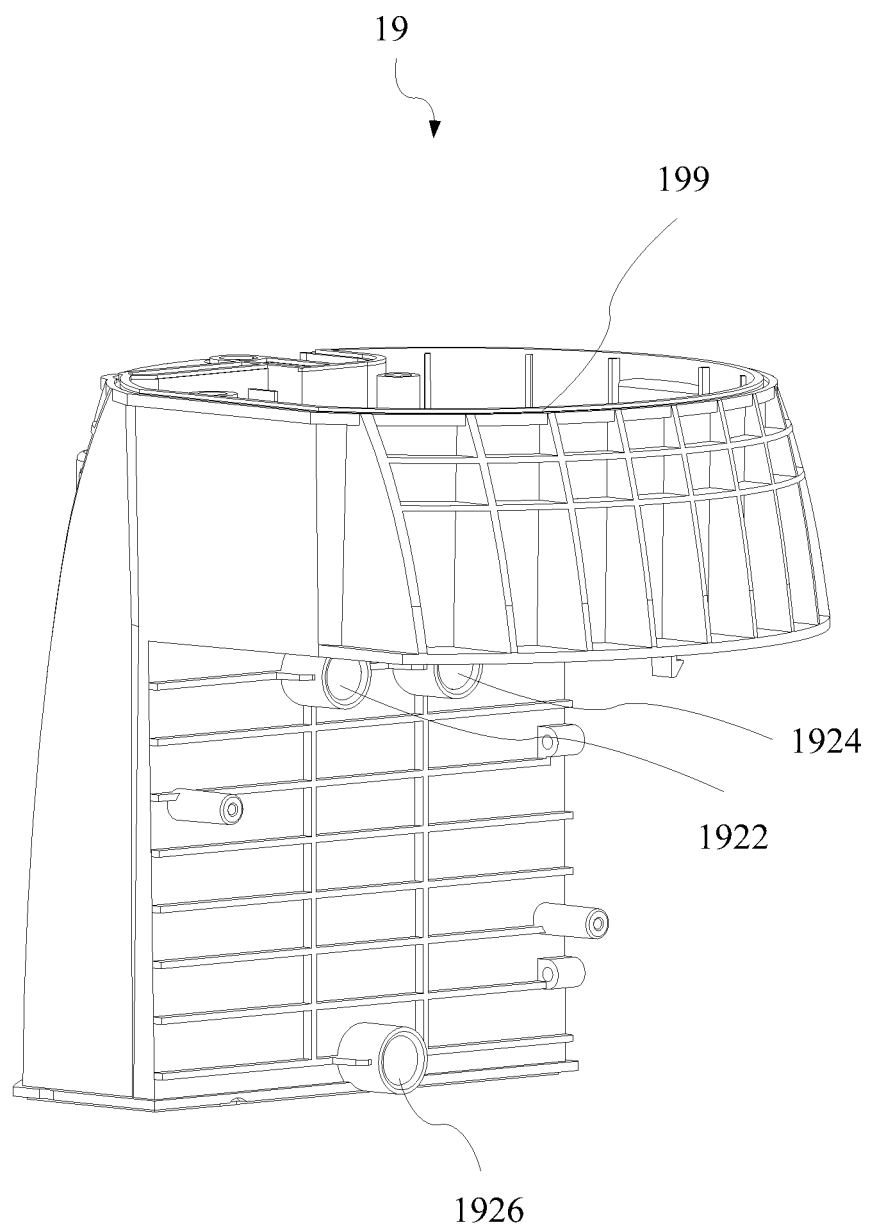
FIG. 11 shows a schematic diagram of one embodiment of the integrated pathway module in the present invention.

Please refer to FIG. 1C, FIG. 2A, FIG. 2B, FIG. 10, and FIG. 11. FIG. 11 shows a schematic diagram of one embodiment of the integrated pathway module in the present invention. In another embodiment, the present invention further provides another electrolysis device 1 comprising the ion exchange membrane electrolytic cell 12 and an integrated pathway module 19. The ion exchange membrane electrolytic cell 12 is configured for electrolyzing water. The ion exchange membrane electrolytic cell 12 comprises the second side S2, the ion exchange membrane 120, the cathode 123, the anode 124, the hydrogen output tube 21, and the oxygen output tube 22. Wherein, the ion exchange membrane 120 is configured between the cathode 123 and the anode 124. Wherein, when the ion exchange membrane electrolytic cell 12 electrolyzes water, the cathode 123 generates hydrogen, and the hydrogen is outputted via the hydrogen output tube 21; the anode 124 generates oxygen, and the oxygen is outputted via the oxygen output tube 22. The integrated pathway module 19 has a water tank 199 and a gas pathway. The water tank 199 is coupled to the ion exchange membrane electrolytic cell 12 for replenishing the water to the ion exchange membrane electrolytic cell 12. Wherein, the top of the water tank 199 is higher than the top of the ion exchange membrane electrolytic cell 12. The gas pathway is coupled to the ion exchange membrane electrolytic cell 12 for transporting the hydrogen. Wherein, the second side S2 of the ion exchange membrane electrolytic cell 12 faces the integrated pathway module 19. The oxygen and the hydrogen are outputted to the gas pathway from the second side S2. The water is inputted to the ion exchange membrane electrolytic cell 12 from the second side S2.

The integrated pathway module 19 further has a hydrogen port 1922, an oxygen port 1924 and a water port 1926. The hydrogen port 1922 is coupled to the hydrogen output tube 21 for inputting the hydrogen generated by the ion exchange membrane electrolytic cell 12 into the integrated pathway module 19. The oxygen port 1924 is coupled to the oxygen output tube 22 for inputting the oxygen generated by the ion exchange membrane electrolytic cell 12 into the integrated pathway module 19. The water port 1926 is coupled to the water tank 199 for outputting the water from the water tank 199 into the ion exchange membrane electrolytic cell 12. Besides, the pre-heating tank 17, the separation tank, and the ports, the inlets, the outlets, or the passways among the devices may be integrated to the integrated pathway module 19.

In the present embodiment, the function, the structural design, and the various changes of the ion exchange membrane electrolytic cell 12 is the same with the ion exchange membrane electrolytic cell 12 in other embodiments. The function, the structural design, and the various changes of other components in the electrolysis device are similar to those in other embodiments. However, the components accommodating and transporting gas and water are integrated to a systematic structure; moreover, the integrated pathway module 19 can be integrally formed. Therefore, the volume of the electrolysis device can be compact, the space in the electrolysis device can be used effectively, and the concern of the pathway breakage can be relieved.

In summary, the present invention provides a water electrolysis device comprising an ion exchange membrane electrolytic cell outputting hydrogen and oxygen from the same side, so the space around the ion exchange membrane electrolytic cell can be used effectively. The electrolysis device further comprises a gas tube, a gas pump, and a gas mixing chamber. The ion exchange membrane electrolytic cell electrolyzes water to generate hydrogen. The hydrogen is transported into the gas tube. The gas pump draws air into gas tube unidirectionally with an angle to dilute the hydrogen in the gas tube. Then the diluted hydrogen is transported into gas mixing chamber and mixed with an atomized gas. After that, the healthy gas is formed and is inhaled by users.

Compare to the prior art, the ion exchange membrane electrolytic cell outputs the hydrogen and the oxygen at the same side. Furthermore, the ion exchange membrane electrolytic cell, the water tank, the gas tube, the fan, the gas pump, the operation panel, the gas mixing chamber, and other devices are configured in the housing within the limited volume. Therefore, the present invention maintains enough hydrogen production and also provides accommodation space within the housing as much as possible. The present invention provides a water electrolysis device which is efficient in using space, safety, small size and low noise, so the electrolysis device can be used conveniently by the user.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A water electrolysis device, comprising:
   a housing comprising a side wall; and
   an ion exchange membrane electrolytic cell within the housing and configured to electrolyze water and generate hydrogen and oxygen, the ion exchange membrane electrolytic cell comprising a first side, a second side corresponding to the first side, an ion exchange membrane, a cathode, an anode, a hydrogen output tube, and an oxygen output tube, the ion exchange membrane being configured between the cathode and the anode; and an integrated water tank module within the housing and coupled to the ion exchange membrane electrolytic cell, the integrated water tank module comprising a water tank configured to supply the water to the ion exchange membrane electrolytic cell;

wherein when the ion exchange membrane electrolytic cell electrolyzes water, the cathode generates hydrogen which is outputted via the hydrogen output tube, and the anode generates oxygen which is outputted via the oxygen output tube;

wherein the hydrogen output tube and the oxygen output tube are coupled to the second side of the ion exchange membrane electrolytic cell and the hydrogen and the oxygen are outputted from the second side of the ion exchange membrane electrolytic cell;

wherein the integrated water tank module receives the hydrogen and the oxygen generated by the ion exchange membrane electrolytic cell through the hydrogen output tube and the oxygen output tube, respectively.

2. The water electrolysis device of claim 1, wherein the anode is between the ion exchange membrane and the second side, and the cathode is between the ion exchange membrane and the first side; the oxygen output tube extends from the area between the ion exchange membrane and the second side to the second side, and penetrates through the second side; and the hydrogen output tube extends from the area between the ion exchange membrane and the first side to the second side, and penetrates through the second side.

3. The water electrolysis device of claim 1, wherein the anode is between the ion exchange membrane and the first side, and the cathode is located between the ion exchange membrane and the second side; the hydrogen output tube extends from the area between the ion exchange membrane and the second side, and penetrates through the second side; and the oxygen output tube extends from the area between the ion exchange membrane and the first side, and penetrates through the second side.

4. The water electrolysis device of claim 1, wherein the ion exchange membrane electrolytic cell comprises a cathode chamber and an anode chamber, the cathode chamber comprises the cathode comprising a cathode conductive plate, a cathode seal plate, and a cathode external plate; the anode chamber comprises the anode comprising an anode conductive plate, an anode seal plate, and an anode external plate.

5. The water electrolysis device of claim 4, wherein the ion exchange membrane electrolytic cell further comprises a water tube configured to penetrate through the cathode external plate, the cathode conductive plate, and the cathode seal plate to communicate the cathode chamber and the water tank; the water tube is configured to replenish the water of the water tank into the cathode chamber.

6. The water electrolysis device of claim 5, further comprising a water gauge configured to detect water level of the water tank.

7. The water electrolysis device of claim 1, wherein the integrated water tank module further comprises a gas tube, and the water electrolysis device further comprises a gas pump, wherein the gas tube is coupled to hydrogen output tube to receive the hydrogen, and the gas pump draws a gas into the gas tube to dilute the hydrogen inside the gas tube.

8. The water electrolysis device of claim 7, further comprising a gas mixing chamber coupled to the gas tube to receive the diluted hydrogen, wherein the gas mixing chamber selectively generates an atomized gas to mix with the hydrogen to form a healthy gas, and the atomized gas is water vapor, atomized solution, volatile essential oil, or any combination thereof.

9. The water electrolysis device of claim 7, wherein the gas pump is coupled to the gas tube via a gas inlet; an angle is formed between a first flowing direction of the gas tube and a second direction of the gas inlet, a linking position between the gas inlet and the gas tube is provided with the angle, and the angle is less than 90 degrees.

10. The water electrolysis device of claim 9, wherein the angle is in a range between 25 degrees and 45 degrees, and the shape of the linking position forms a shape of an arc between the gas inlet and the gas pump.

11. The water electrolysis device of claim 7, further comprising:
a hydrogen concentration detector, coupled to the gas tube and configured to detect whether the hydrogen concentration of the gas tube is in a range between a first threshold and a second threshold, wherein the hydrogen concentration detector generates a first warning signal when the detected hydrogen concentration is higher than the first threshold; and
a controller, coupled to the hydrogen concentration detector, the gas pump, and the ion exchange membrane electrolytic cell, wherein the controller generates a start command to turn on the gas pump when receiving the first warning signal.

12. The water electrolysis device of claim 11, wherein the hydrogen concentration detector generates a second warning signal when the detected hydrogen concentration is higher than the second threshold; the controller generates a stop command to turn off the ion exchange membrane electrolytic cell when receiving the second warning signal.

13. The water electrolysis device of claim 12, wherein the first threshold is 4%, the second threshold is 6%, and the range is from 4% to 6%.

14. The water electrolysis device of claim 1, wherein the ion exchange membrane comprises a membrane body, a cathode catalyst layer, and an anode catalyst layer; the cathode catalyst layer and the anode catalyst layer are respectively located at two sides of the membrane body; the cathode catalyst layer is located at the cathode chamber, and the anode catalyst layer is located at the anode chamber; the anode catalyst layer is one selected from a group consisting of Pt, Ir, Pd, the alloy powder of Pt, carbon, and combinations thereof, the cathode catalyst layer is one selected from a group consisting of Pt, Ir, Pd, the alloy powder of Pt, and combinations thereof, and the membrane body is a Nafion membrane.

15. The water electrolysis device of claim 1, further comprising a power supplier, wherein the power supplier comprises a high power port and a low power port; the electric power outputted from the low power port is less than 50% of the electric power outputted from the high power port; the high power port outputs a first voltage and a first current, and the low power port outputs a second voltage and a second current; and the first voltage is less than the second voltage, and the first current is greater than the second current.

16. The water electrolysis device of claim 1, further comprising an operation panel, wherein the volume of the electrolysis device is less than 8.5 liters, and a hydrogen production rate of the electrolysis device regulated by the operation panel is in a range between 120 mL/min to 600 mL/min.

17. A water electrolysis device, comprising:
an integrated water tank module comprising a water tank, a hydrogen port, an oxygen port, and a water port, wherein the water tank is configured for accommodating water;
an ion exchange membrane electrolytic cell coupled to the integrated water tank module, wherein the ion exchange membrane electrolytic cell comprises an ion exchange membrane, a cathode, an anode, a water tube, a hydrogen output tube, and an oxygen output tube, and the water tube is configured to receive the water; when the ion exchange membrane electrolytic cell electrolyzes the water, the cathode generates hydrogen and the anode generates oxygen; the hydrogen output tube is configured to output the hydrogen to the integrated water tank module via the hydrogen port, the oxygen output tube is configured to output the oxygen and a remained water via the oxygen port, and the water tube is coupled to the water tank to receive the water via the water port; and
wherein, the ion exchange membrane electrolytic cell further comprises a casing, the oxygen output tube, the hydrogen output tube and the water tube extend from the casing of the ion exchange membrane electrolytic cell.

18. The water electrolysis device of claim 17, wherein the integrated water tank module further comprises a pre-heating tank which comprises a water inlet, a water outlet, and an oxygen import tube, the water inlet is coupled to the water tank to receive the water, and the water is outputted from the water outlet, and the remained water is outputted from the oxygen import tube to pre-heat the water of the pre-heating tank; the water of the pre-heating tank is pre-heated to the temperature between 55° C. and 65° C., and the volume of the pre-heating tank is less than that of the water tank.

19. The water electrolysis device of claim 18, wherein the pre-heating tank further comprises a plurality of cooling fins and a second fan, the cooling fins are radially configured on an outside wall of the pre-heating tank, and the second fan is configured on an end of the pre-heating tank to cool the pre-heating tank.

20. A water electrolysis device, comprising:
an ion exchange membrane electrolytic cell configured to electrolyze water, comprising a second side, an ion exchange membrane, a cathode, an anode, a hydrogen output tube, and an oxygen output tube, wherein the ion exchange membrane is configured between the cathode and the anode; when the ion exchange membrane electrolytic cell electrolyzes water, the cathode generates hydrogen which is outputted via the hydrogen output tube, and the anode generates oxygen which is outputted via the oxygen output tube;
an integrated water tank module comprising:
a water tank coupled to the ion exchange membrane electrolytic cell, the water tank being configured to replenish the water to the ion exchange membrane electrolytic cell, wherein the top of the water tank is higher than the top of the ion exchange membrane electrolytic cell; and
a gas pathway coupled to the ion exchange membrane electrolytic cell, the gas pathway being configured to transport the hydrogen; wherein, the second side of the ion exchange membrane electrolytic cell faces the integrated water tank module, the oxygen and the hydrogen are outputted to the gas pathway from the second side, and the water is inputted to the ion exchange membrane electrolytic cell from the second side; and
a gas mixing chamber receiving the hydrogen from the gas pathway, wherein the gas mixing chamber selectively generates an atomized gas to mix with the hydrogen to form a healthy gas, and the atomized gas is water vapor, atomized solution, volatile essential oil, or any combination thereof.

* * * * *